United States Patent [19]

Helquist et al.

[11] Patent Number: 5,587,475
[45] Date of Patent: Dec. 24, 1996

[54] DERIVATIZED VIRGINIAMYCIN $M_1$

[75] Inventors: Paul Helquist, Granger, Ind.; Carlo Cocito, Brussels, Belgium

[73] Assignee: University of Notre Dame, Notre Dame, Ind.

[21] Appl. No.: 444,236

[22] Filed: May 18, 1995

[51] Int. Cl.$^6$ ............... C07D 498/14; A61K 37/00; A61K 37/02
[52] U.S. Cl. .............................................. 540/456
[58] Field of Search ................................. 540/456, 458

[56] References Cited

PUBLICATIONS

Chatterjee et al., "Preparation of Therapeutically Useful Alkylsul≈Fonylpristinamycin $II_B$ Derivatives", U.K. Patent No. 2,206,577; Chem. Abstr. 1989, 110, 231347z.
Chatterjee et al., "Novel Pristinamycin $II_B$ Derivatives, Their Preparation and Pharmaceutical Compositions Containing Them", U.K. Patent 2,206,879A (1989); Chem. Abst. 1989, 111, 39104x.
Bernard et al., "Pharmacokinetics and Suction Blister Fluid Penetration of a Semisynthetic Injectable Streptogramin . . . ", Eur. J. Clin. Microbiol. Infect. Dis. 1994, 13, 768–771.
Corbet et al., "Preparation of Pristinamycin $I_A$ and $II_B$ Derivatives and Antibacterial Compositions Containing Them", Canadian Patent No. 1,231,307 (1988); Chem. Abstr. 1988, 109, 190130g.
Chatterjee et al., "Preparation of (Aminoalkylsulfonyl) pristinamycin Derivatives", Eur. Patent Eur. Pat. Appl. 252720 (1988); Chem. Abstr. 1988, 109, 190867c.
Barriere et al., "Streptogramin Analogs", Expert Opin. Invest. Drugs, 1994, 3, 115–131.
Barriere et al., "Preparation of Pristinamycin $II_B$ Sulfoxide", S. African ZA 8704938 (1988); Chem. Abstr. 1989, 110, 134972s.
Freeman et al., "In Vitro Antimicrobial Susceptibility of Glyco≈peptide, Resistant Enterococci", Diagn. Microbiol. Infec. Dis. 1995, 21, 47–50; Chem. Abstr. 1995, 122, 310503y.
Kermbaum, "Synergistines", Semi. Hop. Paris, 1985, 61, 2365–2371.
Corbet et al., "Synergistin Derivatives and Pharmaceutical Compositions Containing Them", French Pat. 2549065 (1985), Chem. Abstr. 1985, 103, 160861e.
Barriere et al., "Pristinamycin IIB Derivatives", French Pat. 2576022 (1986); Chem. Abstr. 1988, 108, 75854p.
Barriere et al., "Preparation of New Synergistins and Pharmaceutical Compositions Containing Them", Eur. Pat. Appl. EP 248,703 (1987); Chem. Abstr. 1989, 110, 193404f.
Paris et al., "Relations Structure–Activité de Dérivés Semi–Synthétiques du Constituant $P_{IA}$ de la Pristinamycine", Path. Biol. 1985, 33, 493–496.
Aumercier et al., "Dérivés Hydrosodubles du Facteur $I_A$ des Pristinamycines", Path. Biol. 1985, 33, 497–501.
Barriere et al., "Antimicrobial Activity Against *Staphylococcus–aureus* of Semisynthetic . . . ", J. Antimicrob. Chemotherapy 1992, 30, Suppl. A, 1–8.
Aumercier et al., "RP 59500: A Proposed Mechanism for its Bactericidal Activity", J. Antimicrob. Chem. 1992, 30, Suppl. A, 9–14.
Neu et al., "The In Vitro Activity of New Streptogramins, RP 59500, RP 57669 and RP 54476, Alone and in Combination", J. Anti. Chem. 1992, 30, Suppl. A, 83–94.
Chambers, "Studies of RP 59500 In vitro and in a Rabbit Model of Aortic Valve Endocarditis. . .", Antimicrob. Agents Chemother. 1992, 30, Supp. A, 117–122.
Fantin et al., "In Vivo Activities and Penetration of the Two Components of the Strepogramin RP 59500. . .", Antimicrob. Agents Chemother. 1994, 38, 432–437.
Lorian et al., "Ultrastructure Alterations of Staphylococcus aureus Exposed to RP59500", J. Antimicrob. Chemother. 1994, 33, 625–628.
Andrews et al., "The in–vitro Activity of a New Semi–Synthetic Streptogramin Compound, RP 59500, Against Staphylococci and Respiratory Pathogens", J. Antimicrob. Chemother. 1994, 33, 849–853.
Boswell et al., "The Postantibiotic Effect of RP 59500 on Staphyloccocus aureus including Strains with a Raised MBC", J. Antimicrob. Chemother. 1994, 33, 1219–1222.
Barry et al., "In Vitro Activities of a Streptogramin (RP59500), Three Macrolides, and an Azalide Against Four Respiratory Tract Pathogens", Antimicrob. Agents Chemother. 1995, 39, 238–240.
Fantin et al., "Critical Influence of Resistance to Streptogramin B–Type Antibiotics on Activity of RP 59500 (Quinupristin–Dalfopristin). . .", Antimicrob. Agents Chemother., 1995, 39, 400–405.
Entenza et al. , "Treatment of Experimental Endocarditis Due to Erythromycin–Susceptible or–Resistant. . .", Antimicrob. Agents Chemother. 1995, 39, 1419–1424.
L'Heriteau et al., "RP 59500 Prophylaxis of Experimental Endocarditis Due to Erythromycin–Susceptible and –Resistant. . .", Antimicrob. Agents & Chemotherapy, 1995, pp. 1425–1429.
Cocito, "Properties of Virginiamycin–like Antibiotics (Synergimycins), Inhibitors Containing Synergistic Components", Antibotics, vol VI (1983), pp. 296–332.
Vazquez, "The Streptogramin Family of Antibiotics", Antibotics, vo. III (1975), pp.521–534.
Cochito et al.,"Molecular Mechanism of Action of Virginiamycin–like ANtibotics (Synergimycins) on Protein Synthesis. . .", J. Antimicrobial Chemotherapy (1985) 16, Supp. A, pp. 35–52.
Liu et al., "Production of Vernamycin by a Micromonospora", J. Antibiotics (1981), pp. 1515–1516.

(List continued on next page.)

*Primary Examiner*—Robert T. Bond
*Attorney, Agent, or Firm*—Baker & Daniels

[57] ABSTRACT

Derivatized type A virginiamycins having a reactive functionalized side chain, and a process for making the virginiamycin derivatives. The side chain contains a thioether linkage and a reactive group, such as a carboxylate ester or free carboxylic acid group.

22 Claims, 2 Drawing Sheets

OTHER PUBLICATIONS

Biot, "Virginiamycin: Properties, Biosynthesis, and Fermentation", Drugs Pharm. Sci., (1984), pp. 695–720.

Paris et al., "The Chemistry of Pristinamycins", Recent Progress in the Chemical Synthesis of Antibiotics (1990), pp. 185–248.

Di Giambattista et al., "The Molecular Basis of the Inhibitory Activities of Type A and Type B Synergimycins. . .", J. Antimicrobial Chemotherapy (1989), pp. 485–507.

Cocito, "Antibiotics of the Virginiamycin Family, Inhibitors Which Contain Synergistic Components", Microbiological Reviews (1979) pp. 145–198.

Gale et al., "Antibiotics Inhibitors of Ribosome Function", The Molecular Basis of Antibiotic Action (1981), pp. 480–485; p. 529.

Fig. 1. *in vitro* Activity of VM Derivatives 2:
Binding to Ribosomes

FIG. 1

Fig. 2. *in vitro* Activity of VM Derivatives 3:
Binding to Ribosomes

DERIVATIZED VIRGINIAMYCIN M₁

FEDERALLY-SPONSORED RESEARCH

The U.S. Government has a paid-up license in this invention and the right in limited circumstances to require the patent owner to license others on reasonable terms as provided for by the terms of Contract No. NIH 5R01-GM47227 awarded by the National Institutes of Health.

BACKGROUND OF THE INVENTION

This invention relates generally to streptogramin antibiotic derivatives, and more particularly, to derivatives of the streptogramin antibiotic virginiamycin $M_1$, and a process for preparing derivatives of virginiamycin $M_1$.

The streptogramin family of antibiotics includes the ostreogrycins, vernamycins, synergistins, mikamycins, pristinamycins and virginiamycins. These antibiotics generally occur as mixtures of two different classes of active antibiotic compounds, which are commonly referred to as type A (or M) and type B (or S) antibiotics, respectively. Virginiamycin $M_1$ is one member of the type A family of streptogramin antibiotics. Type A streptogramin antibiotics show a very strong synergistic effect when mixed with type B streptogramin antibiotics.

Type A antibiotics, such as virginiamycin M (or A), are polyunsaturated cyclic peptolides, which can be considered as highly modified depsipeptides. These compounds generally have a molecular weight of about 500. Type B antibiotics, such as virginiamycin S (or B) are cyclic hexadepsipeptides unrelated in structure to virginiamycin M. These compounds have a molecular weight of about 800. Although each of the A and B types is an active antibiotic in its own right, when mixed together they exhibit marked synergism of activity. Together, these two classes of naturally occurring antibiotics have been widely used for the treatment of human diseases, for numerous veterinary applications, and as agricultural feed additives.

Although the naturally occurring virginiamycin antibiotics have been effective in particularized uses, more widespread use of these beneficial compounds has been hindered due to certain inherent limitations. A principal limitation on the therapeutic use of the virginiamycins is poor water solubility and distribution characteristics. The poor water solubility of these antibiotics means that they can only be administered orally, and that they are not easily distributed to the affected areas of the body.

Another limitation on the use of virginiamycins is that virginiamycins do not easily form conjugates with other therapeutic agents, which hinders the potential formation of new conjugates having improved and wider ranges of biological activities.

Yet another limitation on the use of these naturally occurring virginiamycins is that it is difficult to attach reactive groups such as affinity labels to the type A antibiotics such as virginiamycin, and at the same time retain the normal antibiotic activity. The ability to attach such groups would allow further study of the mechanism of the antibiotic activity, in order to provide researchers with information that could be used to improve the effectiveness of the antibiotic, to synthesize improved drugs, or to study the structure and function of ribosomes, which are the natural target of these antibiotics.

Although certain derivatives of virginiamycin have been formulated in the past, many of the known derivatives have exhibited a loss of antibacterial activity when compared to the virginiamycin. Although some derivatives have retained a certain level of activity, these derivatives often do not possess a conveniently reactive functional group that can be used for attaching other agents to the antibiotic. The most active derivatives have been obtained by addition of amino-containing thiols to virginiamycin $M_1$, followed by oxidation of the resulting sulfide linkages to sulfoxides and sulfones, and conversion of the amine functions to ammonium salts. Some of these compounds exhibit useful antibacterial activity. A review article by Paris, et al, summarizes much of this work. Paris, et al., "The Chemistry of Pristinamycins", *Recent Progress in the Chemical Synthesis of Antibiotics*, 1990, pp. 183–247.

Prior work by one of the present inventors has demonstrated the use of N-hydroxysuccinimide ester (HSE) as an affinity label with virginiamycin $S_1$ (VS) (U.S. Pat. No. 5,200,394). In this work, the HSE affinity label was activated for binding to ribosomal proteins at 30° C., or permissive conditions. However, such work has not heretofore been successfully employed with virginiamycin $M_1$.

It is desired to provide derivatives of the type A virginiamycin antibiotics having antibiotic activity comparable to the antibiotic activity of the natural virginiamycin. It is further desired to provide such derivatives wherein the solubility and distribution characteristics are improved over the original antibiotic, that are adaptable for inclusion of affinity labels, and that may be conjugated with other therapeutic agents.

SUMMARY OF THE INVENTION

The present invention, in one form thereof, provides a virginiamycin derivative having a reactive functionalized side chain. The reactive functionalized side chain contains a thioether linkage and a reactive group, such as a carboxylate ester or free carboxylic acid group.

The present invention, in another form thereof, comprises a process for preparing a virginiamycin derivative having a reactive functionalized side chain. A side chain containing a thioether linkage and a reactive group is obtained by preparing a suitable ω-mercapto carboxylic acid, and synthesizing a ω-mercapto ester from the ω-mercapto carboxylic acid. The side chain is then attached to said virginiamycin $M_1$ by a Michael addition. The ester derivative may then be hydrolyzed to form an acid derivative.

An object of the present invention is to provide derivatives of virginiamycin $M_1$ having a wider range of use than virginiamycin, yet having an antibiotic activity comparable to that of virginiamycin.

A further object of the present invention is to provide derivatives of virginiamycin $M_1$ having improved solubility and distribution characteristics compared to virginiamycin $M_1$.

Yet another object of the present invention is to provide derivatives of virginiamycin $M_1$ wherein affinity labels may be attached to the reactive side chains of the derivatives.

A still further object of the present invention is to provide derivatives of virginiamycin $M_1$ having a reactive functionalized side chain useful for linking the virginiamycin system to other therapeutic agents for the purpose of forming conjugates having improved and wider ranges of biological activities.

BRIEF DESCRIPTION OF THE DRAWINGS

FIGS. 1 and 2 illustrate the in vitro activities of $VM_1$ derivatives binding to free ribosomes, compared to the activity of virginiamycin.

DETAILED DESCRIPTION OF THE INVENTION

The present invention comprises derivatives of the type A streptogramin antibiotic virginiamycin $M_1$ ($VM_1$), and a process for preparing derivatives of $VM_1$. The inventive derivatives include a reactive functionalized side chain attached to the dehydroproline group of virginiamycin. The functionalized side chain contains a thioether linkage combined with a carboxylate ester or a free carboxylic acid group. Other related reactive groups may also be introduced into the side chain.

The addition of the reactive functionalized side chain to $VM_1$ offers several advantages when compared to the original antibiotic. For example, an affinity label such as HSE may be attached to the reactive functionalized side chain, and activated for binding to ribosomal proteins. Use of such affinity labels permits study of the reaction mechanism of the antibiotic. Under controlled conditions the reactive groups are able to react with components of bacterial ribosomes, which are the targets of this class of antibiotics. The dissociation of the modified virginiamycin.ribosome complexes allows the ribosomal components at the virginiamycin binding site to be identified by affinity labeling. Since the virginiamycins are peptidyl transferase inhibitors, such an approach may be used to identify the components at the catalytic center of the enzyme responsible for peptide bond formation. Such knowledge is of fundamental interest in biochemistry, molecular biology and related fields. Photoaffinity labels such as azidoaromatics may also be attached to the reactive functionalized side chain. Photoaffinity labels are of generally accepted use in this field. In the above cases, a radioactive $^{35}S$ label may also be incorporated to monitor the isolation and characterization of affinity or photoaffinity labelled ribosome components.

The addition of the reactive functionalized side chain may be expected to improve the solubility and distribution characteristics of the antibiotic. Carboxylic acid groups and their derivatives have often been found useful for improving these properties of pharmaceutical agents in general. The length of the side chain in the ester and carboxylic acid may be altered by appropriate choice of starting materials in order to modify the solubility and distribution characteristics of these classes of derivatives. Such alteration of the chain length may also be utilized to modify the reactivity of the affinity labeled derivatives, as well as the biological activity of the conjugates that may be obtained from the ester and carboxyl and related derivatives.

The addition of the reactive functionalized side chain enhances the ability of the ester, carboxyl and related derivatives to be conjugated with other pharmacophores, to thereby improve and extend the ranges of biological activity of the derivatized compounds. Conjugates may be formed with several types of biologically active compounds, such as virginiamycin S, as well as other members of the Type B streptogramin antibiotics. Additional examples include other classes of antibiotics, antineoplastic agents, antiviral agents and antifungal agents. The conjugates formed with other types of antibiotics are especially significant. Such conjugates may exhibit dual mechanisms of action, which may increase efficacy in the case of bacteria that are resistant to simpler antibiotics having only one mode of action.

Each of the side chains is bonded to the $VM_1$ by way of the thioether (sulfide) linkage. The side chain may include saturated n-alkyl, branched alkyl, and cycloalkyl derivatives, and their unsaturated alkene or alkyne derivatives. Such side chains would be substituted with reactive groups, designated below as Z. A representative listing of side chains that may be attached to $VM_1$ according to the inventive process includes:

$-S(CH_2)_nZ$ (n=1 to 20)

$S(CH_2)_mCH[(CH_2)_nCH_3](CH_2)_pZ$ (m=0 to 20, n=0 to 20, p=0 to 20)

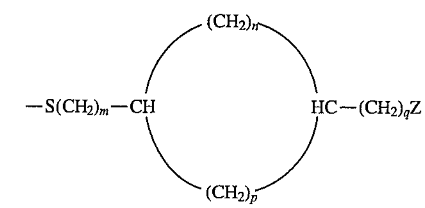

(m = 0 to 10, n = 0 to 10, p = 0 to 10, q = 0 to 10)

The corresponding unsaturated derivatives may likewise be attached to $VM_1$ according to the inventive process. These unsaturated derivatives have adjacent pairs of saturated carbon atoms in the structures shown above replaced by alkene or alkyne units.

The reactive groups Z include the following:

$CO_2CH_2CCl_3$ (2,2,2-trichloroethyl esters), $CO_2(CH_2)_nCH_3$ (n-alkyl esters), $CO_2(CH_2)_mCH[(CH_2)_nCH_3](CH_2)_pCH_3$ (branched alkyl esters), $CO_2(CH_2)_m(CH{=}CH)\ (CH_2)_nH$ (unsaturated alkyl esters), $CO_2H$ (carboxylic acids), $CONH_2$ (primary amides), CONHR (secondary amides, R=saturated or unsaturated n-alkyl or branched alkyl groups as shown for the esters above), and CONRR' (tertiary amides, R and R'=saturated or unsaturated n-alkyl or branched alkyl groups as shown for the esters above)

$CO_2^-M^+$ (carboxylate salts, $M^+$=lithium, sodium, potassium, cesium, magnesium, or calcium cation, with or without other coordinating groups, or ammonium, monoalkylammonium, dialkylammonium, trialkylammonium, or tetraalkylammonium bearing n-alkyl or branched alkyl groups as shown for the esters above, or ammonium salt derivatives of amino acids).

The following reaction sequence illustrates an exemplary process for preparing the inventive derivatives containing a thioether linkage and a carboxylate ester (2) or free carboxylic acid group (3).

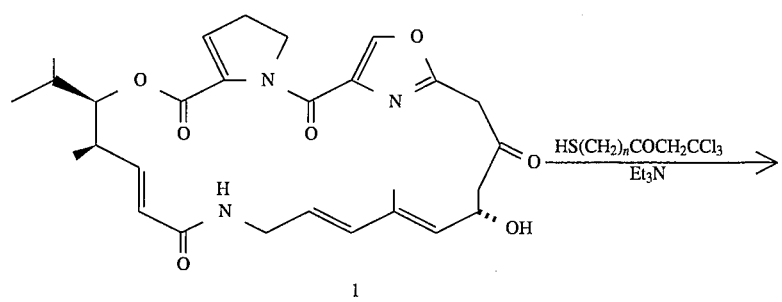
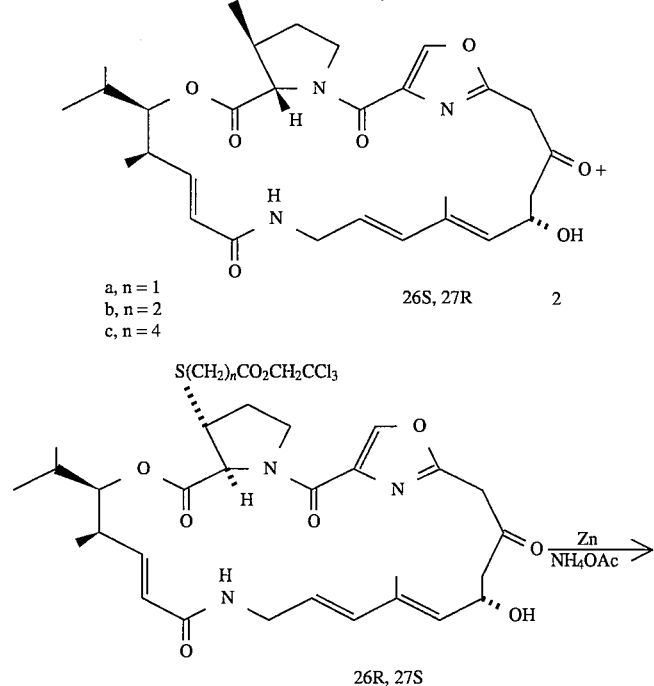
a, n = 1
b, n = 2
c, n = 4
26S, 27R    2
26R, 27S
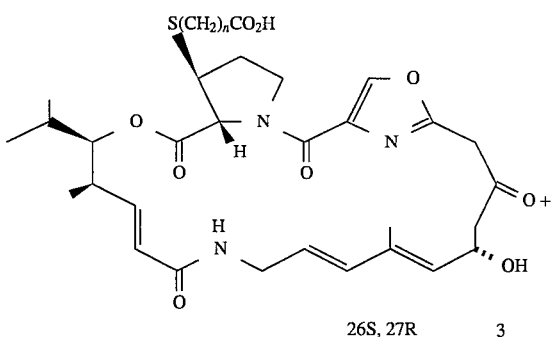
26S, 27R    3
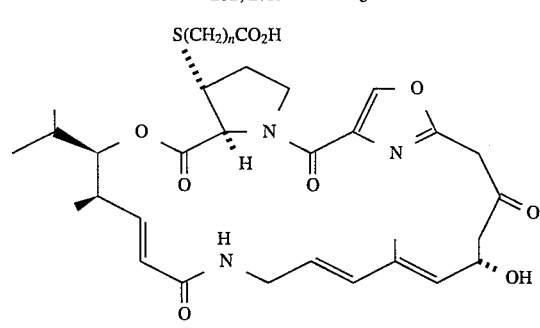
26S, 27R Further details of the process for preparing the virginiamycin derivatives shown in this reaction sequence are provided below:

Isolation of virginiamycin $M_1$

Initially, the virginiamycin $M_1$ ($VM_1$) raw material used in the inventive process is prepared for the addition of the reactive functionalized side chain. Virginiamycin $M_1$ is commercially available in crude form as the agricultural livestock feed additive STAFAC®, manufactured by Smith Kline Beecham, of Exton Pa.

A procedure for purification of $VM_1$ in the crude feed is reported by N. K. Sharma, N. Hosten and M. J. O. Anteunis, "Isolation of Factor A (Virginiamycin $M_1$) and Factor B (Mixture of $VS_1$ and $VS_4$) from a Commercial Feed Additive Formulation," *Bull. Soc. Chim. Belg.*, 1988, 97, 185–192.

A simplified modification of the procedure of *Sharma, et el.* is suitable for use in the invention. In this procedure, 500 g STAFAC® is placed in an Erlenmeyer flask with 3.75 L methylene chloride. The mixture is stirred overnight with a mechanical stirrer. The STAFAC® is filtered, and rinsed with a Buchner funnel under vacuum, giving a cloudy yellow solution. A second filtration is performed through a glass-frit (medium) filter, giving a clear yellow solution. This solution is concentrated in vacuo to give a crude mixture of VM and VS. 10 g of this yellow/brown solid is purified with a medium pressure liquid chromatography (MPLC) column using gradients of 0.5, 1, 1.5, 3, 4, 6 and 8% methyl alcohol in methylene chloride. The fractions are separated by thin layer chromatography, and the fraction containing VM is concentrated with rotary evaporation. The $VM_1$ is then recrystallized using ethyl acetate. 1.105 g of virginiamycin $M_1$ is obtained.

Preparation of a ω-mercapto carboxylic acid

In order to prepare the side chain for addition to the $VM_1$, a suitable ω-mercapto carboxylic acid (thiol acid) is initially prepared. Such acids may be prepared in the laboratory from commercially available ω-bromo carboxylic acids, according to the procedure reported by J. P. Danehy, C. P. Egan, and J. Switalski, *J. Org. Chem.*, 1971, 36, 2530–34. An example of the preparation of a suitable ω-mercapto carboxylic acid, namely 3-mercaptopropionic acid (shown as b in the reaction sequence shown above, wherein n=2), is described:

A 25 mL flask is charged with 1.0 g 3-bromopropionic acid (6.5 mmol), 647 mg thiourea (8.5 mmol), and 5 mL $H_2O$. The flask is fitted with a water-cooled condenser and the mixture is heated at reflux for 2 hours. 5.2 mL aqueous NaOH (2.5M, 13.0 mmol) is added slowly through the condenser and the mixture is refluxed for 1 hour. The reaction mixture is cooled to 0° C., and aqueous $H_2SO_4$ (2M) is added slowly until the mixture becomes acidic (pH<2). The reaction mixture is extracted with diethyl ether ($Et_2O$). The organic layer is then dried with $MgSO_4$ and concentrated invacuo. The thiol acid obtained by this process is a clear oil (99% yield), and is essentially pure. If desired, a radiolabel such as $^{35}S$ may be introduced into the ω-mercapto carboxylic acid by utilizing the commercially-available $^{35}S$ thiourea in this process.

Synthesis of a ω-mercapto ester

The ω-mercapto ester (thiol ester) to be attached to the $VM_1$ is then synthesized by esterification of the corresponding ω-mercapto carboxylic acid. The ω-mercapto carboxylic acid is heated with a reaction mixture comprising an alcohol and an acid catalyst, in the presence of an organic solvent. The organic layer is separated from the reaction layer, and the ω-mercapto ester is separated from the organic layer. An example of the synthesis of a suitable ω-mercapto ester, namely 2',2',2'-trichloroethyl-3-mercaptopropanoate, from the ω-mercapto carboxylic acid prepared above is described:

A 100 mL flask is charged with 1.218 g 3-mercaptopropionic acid (11.5 mmol), 2.188 g p-toluenesulfonic acid monohydrate (11.5 mmol), 9.0 mL 2,2,2-trichloroethanol (93.8 mmol) and 50 mL toluene under a nitrogen atmosphere. The flask is connected to a Dean-Stark apparatus, and the mixture heated to reflux for 3 hr. The reaction is cooled to 23° C., and toluene is removed in vacuo. The residue is poured into $Et_2O$, and washed with water (2×10 ml). The organic layer is dried with $MgSO_4$, and concentrated in vacuo. The resulting oil is distilled via a short path distillation apparatus to remove the excess trichloroethanol (46°–48° C., aspirator pressure). The remaining residue is purified by flash column chromatography (Still, W. C., Kahn, M., Mitra, A., *J. Org. Chem.*, 1978, 43, 2923–2925) or medium-pressure liquid chromatography (Baeckstrom, P., Stridh, K., Li, L., Norin, T., *Acta Chem. Scand.*, 1987, B41, 442) (10% EtOAc in hexanes) to give 2',2',2'-trichloroethyl 3-mercaptopropanoate The ester is obtained as a clear oil (90% yield). Elemental Analysis calculated for $C_5H_7Cl_3O_2S$: C, 25.28%; H, 2.97%. Found: C, 25.17%; H, 2.77%.

Addition of the ω-mercapto ester to $VM_1$

The ω-mercapto ester (thiol ester) is attached to $VM_1$ by a Michael addition. Preferably, the base used in the Michael addition comprises triethylamine, although other tertiary amines or inorganic bases of comparable base strengths are acceptable substitutes. The reaction solvent is preferably methylene chloride, or other suitable solvents unreactive toward the desired ester. Due to the limited solubility of $VM_1$ in methylene chloride, it is preferred that an alcohol co-solvent also be utilized to improve the solubility and reactivity with virginiamycin. To avoid transesterification as a competing side reaction, the alcohol will preferably comprise the same alkoxy group as the ester.

The Michael addition of the ω-mercapto ester 2',2',2'-trichloroethyl-3-mercaptopropanoate to $VM_1$ (shown as b in the reaction sequence provided above, wherein n=2) is carried out according to the following procedure: A 10 mL flask is charged with 0.048 g (0.2 mmol) of the thiol ester, and purged with nitrogen. 1 mL of the solvent, a 5:1 mixture of methylene chloride ($CH_2Cl_2$) and the polar co-solvent trichloroethanol ($CH_2Cl_2:Cl_3CCH_2OH$), is added, followed by 0.020 g triethylamine (0.2 mmol). The mixture is stirred at 23° C. for 15 minutes, and then 52.5 mg VM in 1 ml of the same solvent as above is added. The mixture is then stirred at 23° C. for 6–18 hr. The reaction is concentrated in vacuo, and purified by column chromatography using 4% MeOH in methylene chloride.

Thin layer chromatography (TLC) analysis of the reaction mixture and isolated products (92:4:4 $CH_2Cl_2:MeOH:AcOH$) often showed three spots running very closely which corresponded to the S,R-isomer, the R,S-isomer and $VM_1$.

An alternate Michael addition was carried out utilizing a 1:1 mixture of $CH_2Cl_2:MeOH$ as solvent. With this solvent, the desired trichloroethyl adducts (S,R:R,S 1:1.7) and undesired methyl esters were isolated. The trichloromethyl adducts (26S,27R, 26R,27S) are generally desired because of the removability of this type of ester to give the carboxylic acid derivatives. In this case, the simpler methyl ester group could not be removed without degradation of the VM system. A byproduct of this Michael reaction was the methyl ester adduct, in which the trichloroethyl ester had been transesterified under the reaction conditions. The thiol-trichloroethyl ester was found to undergo transesterification in the solvent mixture of $CH_2Cl_2:MeOH$ with $Et_3N$ at room temperature to give the thiol methyl ester. When the solvent mixture of 5:1 CH$_2$Cl$_2$:Cl$_3$CCH$_2$OH was employed, transesterification of the trichloroethyl ester is prevented. Alternatively, transesterification may be prevented when using a CH$_2$C$_2$/MeOH solvent mixture if the reaction temperature is lowered to −20° C. The ratio of products 26S,27R, 26R,27S (n=2 in the reaction sequence) increased using lower temperatures, giving a 1:4 ratio of the S,R:R,S isomers.

Although a trichloroethyl ester derivative is prepared by the process described above, the inventive concept may also be utilized with other easily cleaved ester groups which are also amenable to the formation of carboxylic acid derivatives. Examples of suitable easily-cleaved ester groups are the 2-(trimethylsilyl)ethyl ester which can be cleaved with fluoride salts, and the allyl ester which can be cleaved in the presence of palladium catalysts.

Cleavage of the ester derivatives

The ester derivatives may then be cleaved to form the acid derivatives. A 5 mL flask is charged with 20 mg of the trichloroethyl ester and 1 mL THF. The reaction mixture is stirred vigorously under ambient atmosphere as 20 mg zinc dust is added, followed immediately by 200 µL aqueous NH$_4$OAc (1M). The resulting opaque light green mixture is stirred for 2–4 hours. A suitable exchange resin such as Dowex® H$^+$ is added, and the mixture is stirred until the solution is a clear green color. The mixture is filtered through a pipette with a cotton plug and rinsed with additional THF. The solution is dried (MgSO$_4$), filtered and concentrated in vacuo. The residue is purified by flash chromatography or MPLC (92:4:4 CH$_2$Cl$_2$:MeOH:AcOH) to give the acid derivative in a 60–95% yield.

Other series of VM$_1$ derivatives may be synthesized in a similar manner. For example, the longer chain (separating the sulfur and carbonyl) 2',2',2'-trichloroethyl 5-mercaptopentanoate may be prepared by transformation of 5-bromopentanoic acid to the thiol acid 5-mercaptopentanoic acid. In this case, the acid may be prepared by charging 5.0 g 5-bromopentanoic acid (27.6 mmol) with 2.732 g thiourea (35.9 mmol) and 30 mL water in a 100 mL flask. The flask was fitted with a water cooled condenser and the mixture was heated at reflux for 3 hours. 18.4 mL aqueous sodium hydroxide (3M, 55.2 mmol) was then added slowly through the condenser and the mixture refluxed for one hour. The reaction was cooled to 0° C., and aqueous sulfuric acid (2M) was added slowly until the mixture became acidic (pH<2). The reaction was extracted with Et$_2$O, and the organic layer was dried (MgSO$_4$) and concentrated invacuo. The thiol acid was essentially pure, and was obtained as a clear oil (98% yield). The thiol ester 2',2',2'-trichloroethyl 5-mercaptopentanoate is synthesized utilizing p-toluenesulfonic acid monohydrate and 2,2,2-trichloroethanol as before. The ester is obtained as a clear oil (50% yield). Elemental analysis calculated for C$_7$H$_{11}$Cl$_3$O$_2$S: C, 31.66%; H, 4.17%. Found: C, 32.00%; H, 4.21%. VM$_1$ was then functionalized with the thiol ester by the Michael addition, to give the derivatives having a 8–35% yield (S,R:R,S 1:1.9). The ester may be cleaved as provided above to give the acid derivative (20–63% yield). This sequence is shown as c above, wherein n=4.

Similarly, the shorter chain thiol ester 2',2',2'-trichloroethyl 2-mercaptoacetate (shown as a in the reaction sequence above, wherein n=1) may be prepared by esterification of the corresponding thiol acid. The thiol ester is obtained as a clear oil (95% yield). Elemental analysis calculated for C$_4$H$_5$Cl$_3$O$_2$S: C, 21.50%; H, 2.25%. Found: C, 21.56%; H, 2.31%. Similarly, the thiol ester may be cleaved to give the acid derivative.

Other n-alkyl, branched alkyl or cycloalkyl ester derivatives of VM$_1$ may be prepared by using the corresponding ester-containing thiols as starting materials, or by separate esterification of the carboxylic acid derivatives. Similarly, amide derivatives may be prepared by using the corresponding amide-containing thiols as starting materials, or by separate amide formation from the carboxylic acid derivatives. The carboxylate salts may also be obtained by treatment of the carboxylic acid derivatives with base, in the presence of the appropriate cation or by cation exchange, utilizing techniques well known in the art.

As stated, allyl ester derivatives may also be prepared by the inventive process. Allyl esters may be beneficial as they have the potential of being more easily cleaved than the trichloroethyl esters. The following examples describe a procedure for preparing allyl ester derivatives:

Preparation of 11-mercaptoundecanoic acid 4 g (15.09 mmol) 11-bromoundecanoic acid is added along with 1.505 g thiourea (19.82 mmol) and 15 ml water to a round botton flask, and the mixture is refluxed for 3 hours. 10.2 ml 3M sodium hydroxide (30.6 mmol) was then added and the mixture was refluxed for one additional hour. The reaction mixture was cooled in an ice bath, and dilute sulfuric acid was added dropwise until the solution had a pH of about 2. The cloudy solution was then extracted with ether (2×25 ml), dried over anhydrous MgSO$_4$, and concentrated under reduced pressure to give a white solid (3.1 g, 94%). $^1$H-NMR (300 MHz, CDCl$_3$) 1.28, m, 10 H; 1.60, m, 7 H; 2.35, t, 2 H, J=7.3 Hz; 2.50, q, 2 H, J =7.5 Hz.

Preparation of allyl 11-mercaptoundecanoate 1.09 g (5 mmol) 11-mercaptoundecanoic acid was placed along with 3 g (51.7 mmol) allyl alcohol, 0.57 g p-toluenesulfonic acid and 40 ml benzene in a round bottom flask and heated for 25 minutes with azeotropic removal of water using a Dean-Stark apparatus. The reaction mixture was then cooled and washed with 10% aqueous sodium bicarbonate solution (3×20 ml). The benzene layer was dried over anhydrous MgSO$_4$, and removal of solvent yielded a colorless oil (0.997 g, 77%). $^1$H-NMR (300 MHz, CDCl$_3$) 1.27, m, 12 H; 1.60, m, 5 H; 2.33, t, 2 H, J=7.5 Hz; 2.51, q, 2 H, J=7.4 Hz; 4.59, dt, 2 H, J=5.7, 1.4 Hz; 5.20–5.39, m, 2 H; 5.85–6.00, m, 1 H; IR (film) 2560 (SH), 1730 (C=O), 1640 cm$^{-1}$ (C=C); EI-MS; 258 (M$^+$).

The allyl ester may then be attached to VM$_1$ by a Michael addition in the manner described above. Allyl esters may be cleaved for the formation of carboxylic acid derivatives with palladium catalysts in a manner well known in the art.

Other allyl esters may be prepared in a similar manner. For example, 8-mercaptooctanoate is prepared from 8-mercaptooctanoic acid as follows:

Preparation of 8-mercaptooctanoic acid 5.0 g 8-bromooctanoic acid (22.4 mmol), 2.24 g thiourea (29.4 mmol) and 22 ml water were placed in a round botton flask, and the mixture was refluxed for 3 hours. 15.1 ml 3M sodium hydroxide was then added and the mixture was refluxed for one additional hour. The reaction mixture was cooled in an ice bath, and dilute sulfuric acid was added dropwise until the solution had a pH of about 2. The cloudy solution was then extracted with ether (2×25 ml), dried over anhydrous MgSO$_4$, and concentrated under reduced pressure to give a white solid (2.52 g, 64%). $^1$H-NMR (300 MHz, CDCl$_3$) 1.37, (m, 7 H); 1.60, (m, 4 H); 2.35, (t, J=7.4 Hz, 2 H); 2.52, (q, J=7.4 Hz, 2 H).

Preparation of allyl -mercaptooctanoate 0.597 g (3.38 mmol) 8-mercaptooctanoic acid was placed along with 2.38 ml (35.05 mmol) allyl alcohol, 0.39 g p-toluenesulfonic acid and 27 ml benzene in a round bottom flask and heated for 25 minutes with azeotropic removal of water using a Dean-Stark apparatus. The reaction mixture was then cooled and washed with 10% aqueous sodium bicarbonate solution (3×20 ml). The benzene layer was dried over anhydrous $MgSO_4$, and solvent was removed under reduced pressure to yield a colorless oil (0.496 g, 68%). $^1$H-NMR (300 MHz, $CDCl_3$) 1.21, (m, 7 H), 1.58 (m, 4 H); 2.24, (t, J=7.4 Hz, 2 H); 2.41, (q, J=7.4 Hz, 2 H) ; 4.48, d, J=5.7 Hz, 2 H; 5.10-5.21, (m, 2 H) ; 5.78–5.90, (m, 1 H); FAB-MS: m/e 217 ($M^+$+1).

pathway may allow greater flexibility by (1) providing synthetic intermediates having improved solubility and stability for carrying out various further reactions on the ester or carboxylic acid side chain, and (2) permitting the introduction of affinity labels on the carboxylic acid or ester side chain that would normally be too reactive toward the free C-14 hydroxyl group. A representative sequence of reactions and the corresponding procedures are shown below.

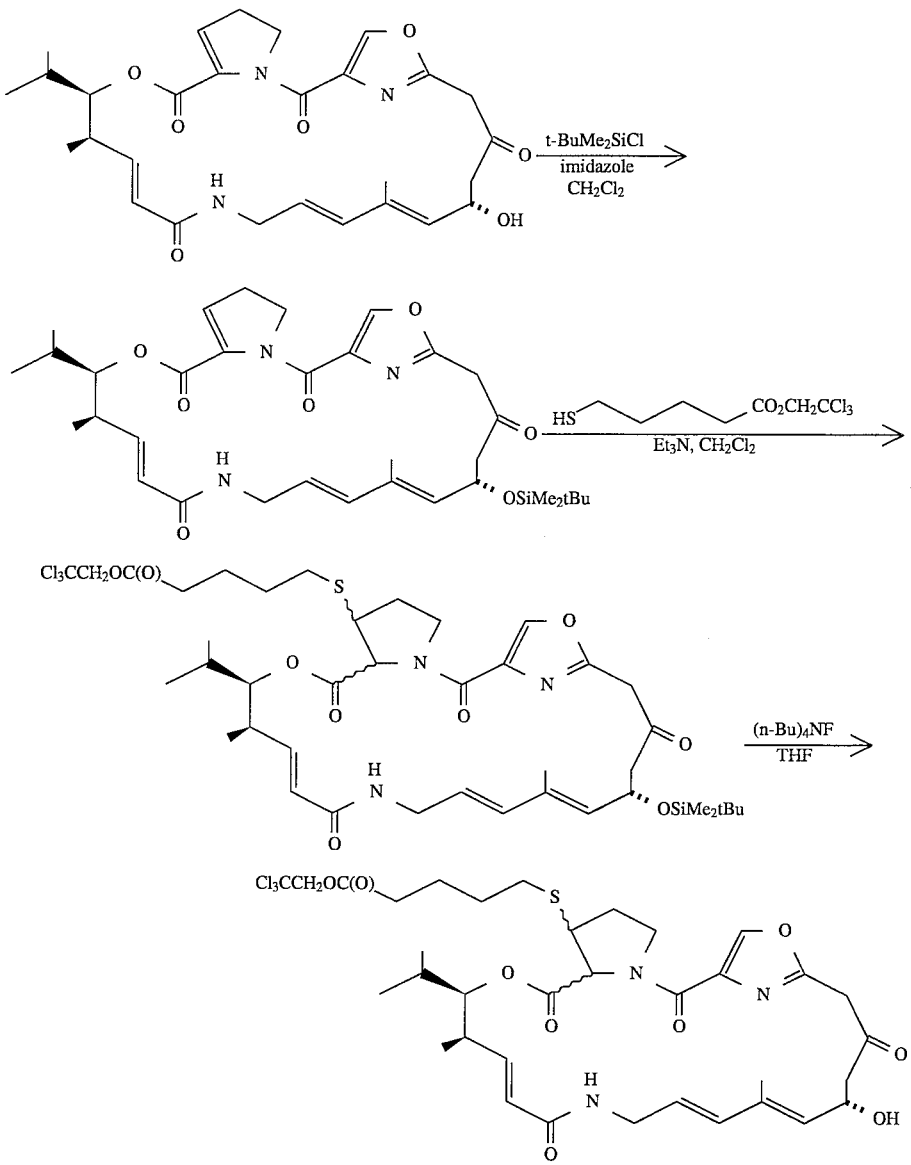

A modified procedure for the synthesis of the VM derivatives involves the prior protection of the C-14 hydroxyl group as a silyl ether. Previous studies of silylations of this type are summarized in a review article by Paris, et al., "The Chemistry of pristinamycins", *Recent Progress in the Chemical Synthesis of Antibiotics*, described above. Any of several silyl derivatives may be used, but the tert-butyldimethylsilyl group is presently preferred. The ω-mercapto ester can then be added to the dehydroproline moiety using the procedure described above. The silyl group may then be cleaved with a fluoride salt to give the same overall product as obtained by the procedure described above. This modified Synthesis of VM-OSi-t-BuMe2.

0.78 g imidazole (11 mmol), 0.86 g tert-butyldimethylsilyl chloride (5.7 mmol), and 40 mL methylene chloride are placed in a flask and cooled to 0° C. To this solution is added a solution of virginiamycin (VM, 1.0 g, 1.9 mmol) dissolved in methylene chloride (20 mL). The reaction mixture is stirred for 3 hours at 25° C. and then quenched with 30 mL water. The mixture is extracted with two 35 mL portions of methylene chloride, and the combined extracts are dried over anhydrous magnesium sulfate and concentrated by rotary evaporation to yield 1.05 g (86%) of the product as a crystalline solid. Preparation of silyl derivatives is also discussed in the previously cited review article by Paris, et al.

Synthesis of Thiol Adduct of VM-OSi-t-BuMe2.

0.066 g of the preceding silyl-protected VM (0.10 mmol) is placed in a flask with 0.2 mL trichloroethanol or methylene chloride at 25° C. under a nitrogen atmosphere, and 0.051 g of the ω-mercapto ester $HS(CH_2)_4CO_2CH_2CCl_3$ (0.2 mmol) is added. Stirring is begun, and then 0.031 g triethylamine (42 μL, 0.3 mmol) is added. The reaction mixture is stirred at 25° C. for 6 hours. After rotary evaporation of the solvent, the crude product is purified by flash or medium-pressure liquid chromatograph (MPLC) on silica gel using 2:1 ethyl acetate:hexane to yield 0.078 g (77%) of the product as a crystalline solid.

Removal of the Silyl Group from the Thiol Adduct of VM-OSi-t-BuMe$_2$.

To 0.053 g of the preceding thiol adduct (0.058 mmol) in a 5 mL round bottom flask is added 1 mL tetrahydrofuran, followed by 0.065 mL of a 1M solution of tetra-n-butylammonium fluoride in tetrahydrofuran at 25° C. The reaction mixture is stirred at 25° C. for two hours. Then, the tetrahydrofuran is removed by rotary evaporation, 5 mL water is added, and the mixture is extracted with methylene chloride. The organic layer is washed with water, dried over anhydrous magnesium sulfate, and concentrated by rotary evaporation to give 0.024 g (52%) of the product as a light yellow liquid as a mixture of two diastereomers. This product was identical ($^1$H NMR) to that obtained by the previously described direct addition of the ω-mercapto ester to the unprotected VM.

The diastereomeric derivatives resulting from the use of the ω-mercapto esters of the present invention display dramatic differences in conformation which may be observed in the $^1$H NMR spectra of the compounds. The pure diastereomers may be obtained by flash or medium pressure liquid chromatography (MPLC) using silica gel with 4% methanol in methylene chloride. The $^1$H NMR spectra of the 26S,27R diastereomers showed a great deal of similarity to the spectrum of VM$_1$, suggesting a similarity in conformation. The $^1$H NMR spectra of the 26R,27S diastereomers, however, were marked by striking dissimilarities compared to the spectrum of VM$_1$. Closely related conformational effects were also discussed in the article by Paris et al.

The synthesized derivatives of the present invention have been tested for antibacterial activity (in solid and liquid medium), ribosome binding affinity and synergistic activity with virginiamycin S. The tests for biological activity were carried out both in vivo and in vitro. The in vivo tests were carried out using *Micrococcus luteus* as the test organism with the VM$_1$ derivatives alone (without VS$_1$). Minimum inhibitory concentrations (MIC values) were determined on agar broth plates by standard microbiological procedures, with a range of concentrations of the VM derivatives applied to the plates. The in vitro tests of the VM derivatives were performed together with VS$_1$, and took advantage of the unique fluorescence (F) inherent in VS$_1$. The results are summarized in the following tables, wherein the activities are compared to virginiamycin (VM$_1$).

| in vivo Activity of VM$_1$-Ester Derivatives, M.I.C. on *M. luteus* | | | | | | | |
|---|---|---|---|---|---|---|---|
| Concentration | a | | b | | c | | |
| (μg/mL) | S,R | R,S | S,R | R,S | S,R | R,S | VM$_1$ |
| 128 | − | − | − | − | − | − | − |
| 32 | − | − | − | − | − | − | − |
| 16 | + | − | − | − | − | − | − |
| 8 | + | − | + | − | + | − | − |
| 4 | + | − | + | − | + | + | − |
| 2 | + | − | + | − | + | + | − |
| 1 | + | − | + | − | + | + | − |
| 0.5 | + | − | + | + | + | + | − |
| 0.25 | + | + | + | + | + | + | − |
| 0.125 | + | + | + | + | + | + | − |
| 0.0625 | + | + | + | + | + | + | + |

*M. luteus* in L-Broth, 18 h at 37° C. with shaking.
(+) indicates multiplication of bacteria.

| in vivo Acitivity of VM$_1$-Carboxylic Derivatives, M.I.C. on *M. luteus* | | | | | | | |
|---|---|---|---|---|---|---|---|
| Concentration | a | | b | | c | | |
| (μg/mL) | S,R | R,S | S,R | R,S | S,R | R,S | VM$_1$ |
| 128 | + | − | + | − | − | − | − |
| 32 | + | − | + | + | − | − | − |
| 16 | + | + | + | + | − | − | − |
| 8 | + | + | + | + | − | − | − |
| 4 | + | + | + | + | − | − | − |
| 2 | + | + | + | + | − | − | − |
| 1 | + | + | + | + | − | − | − |
| 0.5 | + | + | + | + | − | − | − |
| 0.25 | + | + | + | + | + | + | − |
| 0.125 | + | + | + | + | + | + | − |
| 0.0625 | + | + | + | + | + | + | + |

*M. luteus* in L-Broth, 18 h at 37° C. with shaking.
(+) indicates multiplication of bacteria.

| in vitro Activity of VM$_1$-Ester Derivatives | | | |
|---|---|---|---|
| Substrate | $k_{obs}$ (sec$^{-1}$) | t/2 (sec) | Binding to Ribosomes |
| VM | 0.068 | 10.2 | ++++ |
| 26S, 27R-a | * | | − |
| 26R, 27S-a | 0.019 | 35.6 | +++ |
| 26S, 27R-b | 0.0009 | 721 | + |
| 26R, 27S-b | 0.021 | 32.7 | +++ |
| 26S, 27R-c | * | | − |
| 26R, 27S-c | 0.020 | 34.1 | +++ |

(*) too small to be measured. t/2 is very large

| in vitro Activity of VM$_1$-Carboxylic Acid Derivatives | | | |
|---|---|---|---|
| Substrate | $k_{obs}$ (sec$^{-1}$) | t/2 (sec) | Binding to Ribosomes |
| VM | 0.068 | 10.2 | ++++ |
| 26S, 27R-a | * | | − |
| 26R, 27S-a | .00047 | 1487 | + |
| 26S, 27R-b | * | | − |
| 26R, 27S-b | 0.003 | 229 | ++ |
| 26S, 27R-c | 0.015 | 46 | +++ |
| 26R, 27S-c | 0.019 | 38.7 | +++ |

(*) too small to be measured. t/2 is very large

Using spectrofluorometry, an increase in fluorescence can be measured when ribosomes are added to a VS$_1$ solution.

Erythromycin is known to bind at the same position on the ribosome (50-S subunit) as $VS_1$, and when it is added to the $VS_1$/ribosomal mixture, a decrease in fluorescence is seen. If $VM_1$ is added to the $VS_1$/ribosomal/erythromycin mixture, an increase in fluorescence can be measured. Presumably, a conformational change of the ribosomes occurs upon binding of $VM_1$, which allows $VS_1$ to bind preferentially and releases erythromycin from the ribosomes. The $VM_1$ derivatives would also display this type of behavior if they bind to the ribosomes. The results of the in vitro tests for the trichloroethyl derivatives are shown in FIG. 1, and the results of the in vitro tests for the acid derivatives are shown in FIG. 2.

With reference to the reaction sequence shown above, in almost all cases, the 26R,27S isomer (the major isomer) is more active both in vivo and in vitro than the 26S,27R isomer, except for acid derivatives c, wherein n=4, which display nearly identical activity invivo andin vitro. The major addition products (the 26R,27S diastereomers), which have conformations which do not resemble the parent compound $VM_1$, were found to have the higher activity. The derivatives which displayed good invivo activity also generally displayed good in vitro activity, except for the derivatives c, wherein n=4 as mentioned above. It is significant that these derivatives display in vitro activity and are, therefore, suitable candidates for ribosomal binding studies with a radiolabel or photoaffinity label present in the compound.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A compound having the formula

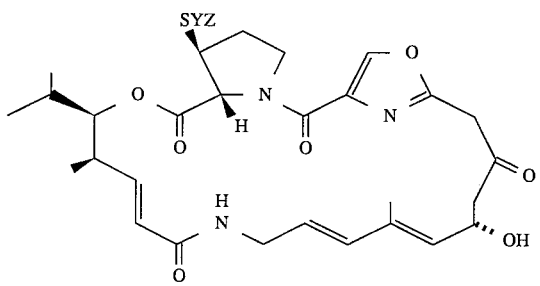

in which Y represents one of $(CH_2)_n$ (n=1 to 20), $(CH_2)_m CH[(CH_2)_n CH_3](CH_2)_p$ (m=0 to 20, n=0 to 20, p=0 to 20), and

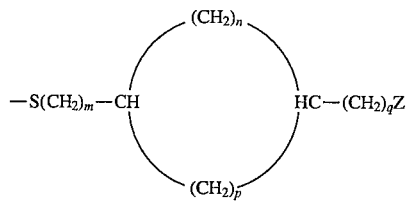

(m = 0 to 10, n = 0 to 10, p = 0 to 10, q = 0 to 10)

or unsaturated derivatives thereof wherein adjacent pairs of saturated carbon atoms are replaced by alkene or alkyne units; and in which Z represents one of $CO_2CH_2CCl_3$, $CO_2(CH_2)_n CH_3$, $CO_2(CH_2)_m CH[(CH_2)_n CH_3](CH_2)_p CH_3$, $CO_2(CH_2)_m (CH=CH)(CH_2)_n H$, $CO_2H$, $CONH_2$, $CONHR$ (R=saturated or unsaturated n-alkyl or branched alkyl as shown for the esters above), $CONRR'$ (R and R'=saturated or unsaturated n-alkyl or branched alkyl as shown for the esters above), and $CO_2^- M^+$ ($M^+$=lithium, sodium, potassium, cesium, magnesium, or calcium cation, with or without other coordinating groups, or ammonium, monoalkylammonium, dialkylammonium, trialkylammonium, or tetraalkylammonium bearing n-alkyl or branched alkyl groups as shown for the esters above, or ammonium salt derivatives of amino acids), including isomeric forms and mixtures thereof.

2. A process for preparing a virginiamycin derivative of the formula

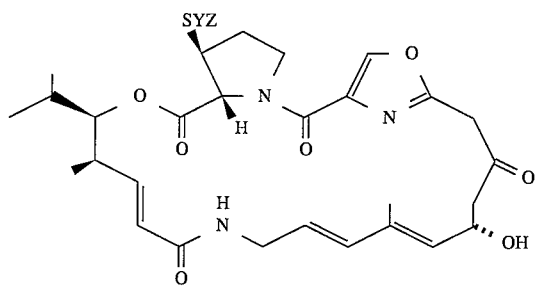

and isomeric forms and mixtures thereof, in which S represents a sulfur atom, Y represents one of $(CH_2)_n$ (n=1 to 20), $(CH_2)_m CH[(CH_2)_n CH_3](CH_2)_p$ (m=0 to 20, n=0 to 20, p=0 to 20), and

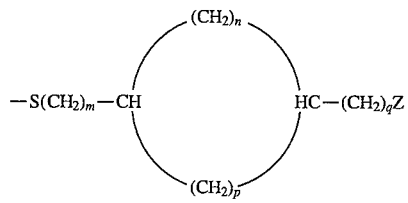

(m = 0 to 10, n = 0 to 10, p = 0 to 10, q = 0 to 10)

(m=0 to 10, n=0 to 10, p=1 to 10, q=0 to 10), or unsaturated derivatives thereof wherein adjacent pairs of saturated carbon atoms are replaced by alkene or alkyne units; and Z represents one of $CO_2CH_2CCl_3$, $CO_2(CH_2)_n CH_3$, $CO_2(CH_2)_m CH[(CH_2)_n CH_3](CH_2)_p CH_3$, $CO_2(CH_2)_m (CH=CH)(CH_2)_n H$, $CO_2H$, $CONH_2$, $CONHR$ (R=saturated or unsaturated n-alkyl or branched alkyl as shown for the esters above), $CONRR'$ (R and R'=saturated or unsaturated n-alkyl or branched alkyl as shown for the esters above), and $CO_2^- M^+$ ($M^+$=lithium, sodium, potassium, cesium, magnesium, or calcium cation, with or without other coordinating groups, or ammonium, monoalkylammonium, dialkylammonium, trialkylammonium, or tetraalkylammonium bearing n-alkyl or branched alkyl groups as shown for the esters above, or ammonium salt derivatives of amino acids), comprising:

reacting a ω-mercapto ester having the formula SYZ, wherein S, Y and Z are as defined above, with a virginiamycin $M_1$ sample having the formula:

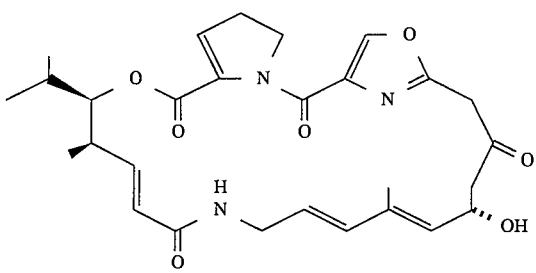

in an organic solvent in the presence of a base, said reaction occurring under reaction conditions conducive for attachment of the SYZ side chain to said virginiamycin $M_1$ via a Michael addition.

3. The process of claim 2, wherein the virginiamycin derivative comprises mixtures of diastereomers of said derivative, said method further comprising the step of separating the virginiamycin derivative into its isomers.

4. The process of claim 3, wherein the virginiamycin derivative is separated into its isomers by flash chromatography or medium pressure liquid chromatography.

5. The process of claim 2, wherein Z comprises a cleavable ester.

6. The process of claim 5, wherein said ester comprises a 2,2,2-trichloroethyl ester.

7. The process of claim 2, wherein said ω-mercapto ester is prepared by:

providing a ω-mercapto carboxylic acid capable of being converted to a ω-mercapto ester; and heating said ω-mercapto carboxylic acid under reaction conditions conducive for esterification of said ω-mercapto carboxylic acid to said ω-mercapto ester [from said ω-mercapto carboxylic acid].

8. The process of claim 7, wherein said heating step comprises:

heating said ω-mercapto carboxylic acid in the presence of a reaction mixture comprising an alcohol that forms a clearable ester with said ω-mercapto carboxylic acid, an acid catalyst, and an organic solvent; and wherein said process further includes the steps of separating the organic layer from the reaction mixture, and recovering the ω-mercapto ester from the organic layer.

9. The process of claim 8, wherein said alcohol comprises trichloroethanol or allyl alcohol.

10. The process of claim 8, wherein said acid catalyst comprises p-toluenesulfonic acid.

11. The process of claim 8, wherein said organic solvent comprises toluene.

12. The process of claim 2, wherein said base comprises triethylamine or other tertiary amines or related bases having base strengths comparable to the base strength of triethylamine.

13. The process of claim 2, wherein said solvent comprises a mixture of methylene chloride, and an alcohol.

14. The process of claim 13, wherein the alcohol includes the same carboalkoxy group of the ester.

15. The process of claim 13, wherein said solvent comprises a 5:1 mixture $CH_2Cl_2$:$Cl_3CCH_2OH$.

16. The process of claim 7, wherein the sulfur component of said ω-mercapto carboxylic acid comprises $^{35}S$.

17. The process of claim 7, wherein said ω-mercapto ester comprises one of 2',2',2'-trichloroethyl 2-mercaptoacetate, 2',2',2'-trichloroethyl 3-mercaptopropanoate and 2',2',2'-trichloroethyl 5-mercaptopropanoate.

18. A process for preparing a virginiamycin derivative of the formula

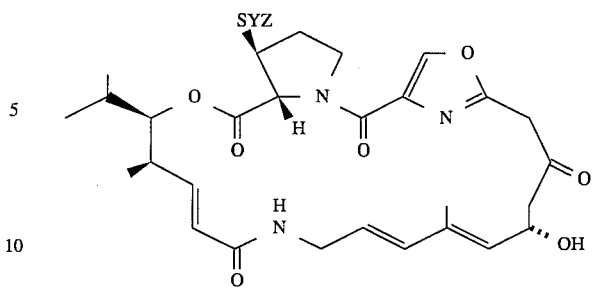

and isomeric forms and mixtures thereof, in which S represents a sulfur atom, Y represents one of $(CH_2)_n$ (n=1 to 20), $(CH_2)_m CH[(CH_2)_n CH_3](CH_2)_p$ (m=0 to 20, n=0 to 20, p=0 to 20), and

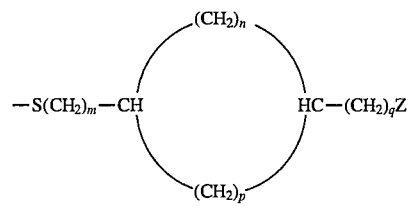

(m = 0 to 10, n = 0 to 10, p = 0 to 10, q = 0 to 10)

(m=0 to 10, n=0 to 10, p=1 to 10, q=0 to 10), or unsaturated derivatives thereof wherein adjacent pairs of saturated carbon atoms are replaced by alkene or alkyne units; and Z represents one of $CO_2CH_2CCl_3$, $CO_2(CH_2)_n CH_3$, $CO_2(CH_2)_m CH[(CH_2)_n CH_3](CH_2)_p CH_3$, $CO_2(CH_2)_m (CH=CH)(CH_2)_n H$, $CO_2H$, $CONH_2$, $CONHR$ (R=saturated or unsaturated n-alkyl or branched alkyl as shown for the esters above), $CONRR'$ (R and R'=saturated or unsaturated n-alkyl or branched alkyl as shown for the esters above), and $CO_2^- M^+$ ($M^+$=lithium, sodium, potassium, cesium, magnesium, or calcium cation, with or without other coordinating groups, or ammonium, monoalkylammonium, dialkylammonium, trialkylammonium, or tetraalkylammonium bearing n-alkyl or branched alkyl groups as shown for the esters above, or ammonium salt derivatives of amino acids), comprising:

reacting a virginiamycin $M_1$ sample having the formula

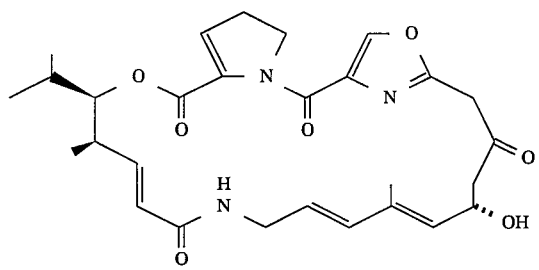

with a silyl ether under conditions conducive for attaching said silyl ether to the C-14 hydroxyl group of said virginiamycin $M_1$ sample, thereby obtaining a C-14 protected virginiamycin $M_1$ sample;

reacting a ω-mercapto ester having the formula SYZ, wherein S, Y and Z are as defined above, with said C-14 protected virginiamycin $M_1$ sample in an organic solvent in the presence of a base under reaction conditions conducive for attachment of the SYZ side chain to said virginiamycin $M_1$; and removing said silyl ether from said C-14 hydroxyl group.

19. The process of claim 18, wherein said silyl ether comprises tert-butyldimethylsilyl.

20. The process of claim 18, wherein said silyl ether is removed from said C-14 hydroxyl group of said virginiamycin derivative by adding a fluoride salt to said virginiamycin derivative; and reacting said fluoride salt with said virginiamycin derivative having said silyl ether attached to said C-14 hydroxyl group under conditions conducive for cleaving said silyl ether from said virqiniamycin derivative.

21. The process of claim 2, wherein the acid derivatives of virginiamycin $M_1$ are prepared from the ester derivatives by cleaving said ester derivatives in the presence of THF and zinc dust or palladium catalysts.

22. The process of claim 2, wherein Z comprises an allyl ester.

* * * * *

UNITED STATES PATENT AND TRADEMARK OFFICE
CERTIFICATE OF CORRECTION

PATENT NO. : 5,587,475
DATED : December 24, 1996
INVENTOR(S) : Paul Helquist, et al.

It is certified that error appears in the above-indentified patent and that said Letters Patent is hereby corrected as shown below:

Claim 7, column 17, beginning on line 33 and continuing on line 34, after "ester", delete "[from said w-mercapto carboxylic acid]."

Claim 8, column 17, line 39, replace "clearable" with --cleavable--.

Claim 20, column 19, line 9, replace "virqiniamycin" with --virginiamycin--.

Signed and Sealed this

Twenty-second Day of April, 1997

Attest:

BRUCE LEHMAN

*Commissioner of Patents and Trademarks*

*Attesting Officer*